(12) United States Patent
Beerwerth et al.

(10) Patent No.: US 10,485,984 B2
(45) Date of Patent: Nov. 26, 2019

(54) SKIN TREATMENT DEVICE

(71) Applicant: Braun GmbH, Kronberg (DE)

(72) Inventors: Frank Beerwerth, Kaltenholzhausen (DE); Christian Neyer, Eschborn (DE); Felix Heinemann, Frankfurt am Main (DE); Dalibor Dadic, Koenigstein (DE); Uwe Bielfeldt, Bad Soden (DE)

(73) Assignee: Braun GMBH, Kronberg (DE)

( * ) Notice: Subject to any disclaimer, the term of this patent is extended or adjusted under 35 U.S.C. 154(b) by 183 days.

(21) Appl. No.: 15/612,153

(22) Filed: Jun. 2, 2017

(65) Prior Publication Data

US 2017/0348544 A1 Dec. 7, 2017

(30) Foreign Application Priority Data

Jun. 7, 2016 (EP) .................................. 16173408

(51) Int. Cl.
*A61N 5/06* (2006.01)
*A61B 18/20* (2006.01)
*A61B 18/00* (2006.01)

(52) U.S. Cl.
CPC .......... *A61N 5/0617* (2013.01); *A61B 18/203* (2013.01); *A61N 5/0616* (2013.01); *A61B 2018/0047* (2013.01); *A61B 2018/00476* (2013.01); *A61B 2018/00827* (2013.01); *A61N 2005/0628* (2013.01); *A61N 2005/0629* (2013.01); *A61N 2005/0643* (2013.01); *A61N 2005/0644* (2013.01); *A61N 2005/0651* (2013.01); *A61N 2005/0652* (2013.01); *A61N 2005/0659* (2013.01); *A61N 2005/0663* (2013.01)

(58) Field of Classification Search
None
See application file for complete search history.

(56) References Cited

U.S. PATENT DOCUMENTS

| | | | |
|---|---|---|---|
| 5,396,893 A | * | 3/1995 | Oberg ................ A61B 5/02416 600/484 |
| 5,445,608 A | * | 8/1995 | Chen .................... A61N 5/0601 604/19 |
| 5,634,711 A | | 6/1997 | Kennedy et al. |

(Continued)

FOREIGN PATENT DOCUMENTS

WO        WO 93/03793        3/1993

OTHER PUBLICATIONS

European search report dated Dec. 7, 2016.

*Primary Examiner* — Carl H Layno
*Assistant Examiner* — Manolis Pahakis
(74) *Attorney, Agent, or Firm* — Ronald Terk Sia; Kevin C. Johnson

(57) ABSTRACT

The present disclosure is concerned with a skin treatment device having at least a first LED, at least a first controllable current source, in particular a first controllable constant current source, for driving the first LED, a control unit for controlled switching of at least the first controllable current source between a first state in which current is provided to the first LED and a second state in which no current is provided to the first LED, and at least a first current sensor that is connected or connectable with the first LED so that the first current sensor and the first LED form a current path at least in the second state of the first controllable current source.

16 Claims, 8 Drawing Sheets

(56) References Cited

U.S. PATENT DOCUMENTS

| | | | |
|---|---|---|---|
| 6,074,382 A * | 6/2000 | Asah | A61B 18/203 |
| | | | 606/10 |
| 9,559,781 B2 * | 1/2017 | Sattler | H05B 33/0827 |
| 2004/0112114 A1 * | 6/2004 | Penney | G08B 29/145 |
| | | | 73/1.01 |
| 2005/0219229 A1 * | 10/2005 | Yamaguchi | G06F 3/0412 |
| | | | 345/173 |
| 2006/0016959 A1 * | 1/2006 | Nishimura | G01J 3/10 |
| | | | 250/205 |
| 2009/0099499 A1 * | 4/2009 | Persin | A61N 5/062 |
| | | | 604/20 |
| 2010/0117958 A1 * | 5/2010 | Liao | G06F 3/0386 |
| | | | 345/158 |
| 2010/0182294 A1 | 7/2010 | Roshan et al. | |
| 2010/0196343 A1 * | 8/2010 | O'Neil | A61B 18/203 |
| | | | 424/94.4 |
| 2011/0069094 A1 * | 3/2011 | Knapp | G09G 3/2003 |
| | | | 345/690 |
| 2012/0157804 A1 * | 6/2012 | Rogers | A61B 5/0422 |
| | | | 600/345 |
| 2013/0190845 A1 * | 7/2013 | Liu | A61N 5/0616 |
| | | | 607/90 |
| 2014/0128941 A1 * | 5/2014 | Williams | A61N 5/06 |
| | | | 607/88 |
| 2014/0214136 A1 | 7/2014 | Liu et al. | |
| 2014/0236265 A1 | 8/2014 | O'Neil et al. | |
| 2015/0231408 A1 * | 8/2015 | Williams | A61N 5/06 |
| | | | 607/88 |
| 2016/0325109 A1 * | 11/2016 | Knaus | A61N 5/06 |
| 2017/0143985 A1 * | 5/2017 | Degenaar | A61N 5/0601 |
| 2019/0003898 A1 * | 1/2019 | Dehkhoda | G01K 7/01 |

\* cited by examiner

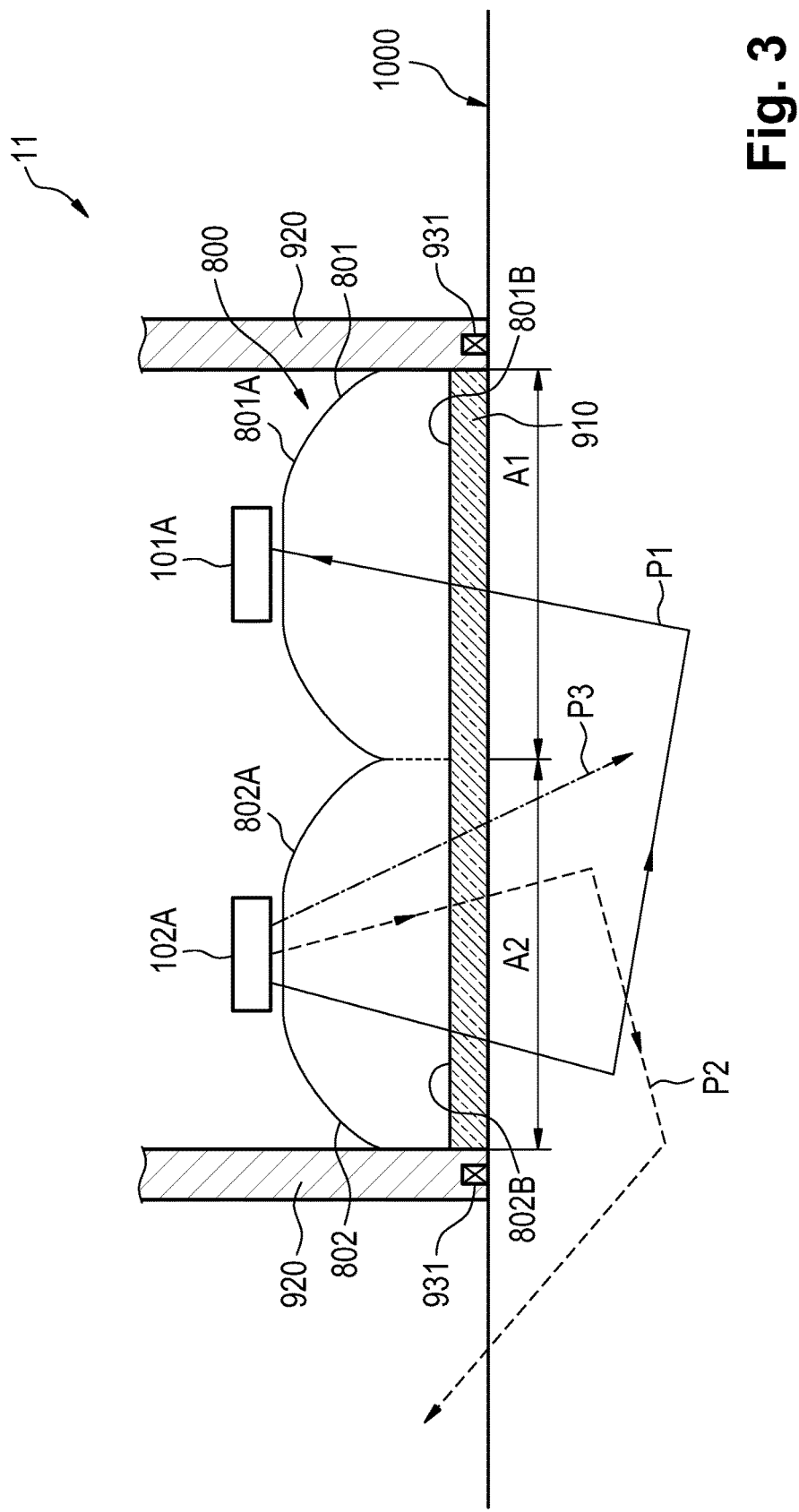

SKIN TREATMENT DEVICE

FIELD OF THE INVENTION

The present invention is concerned with a skin treatment device comprising at least a first LED.

BACKGROUND OF THE INVENTION

It is known that light can be used for medical and cosmetic treatment, e.g. ranging from phototherapy of jaundice to light induced coagulation of hair roots for cosmetic hair removal. Home use devices are on the market for light treatment of a user's skin, e.g. for acne or wrinkle treatment, but also for cosmetic hair removal. In particular for cosmetic hair removal, the light intensity applied to the skin in a relatively short time span (e.g. below 500 ms) must be relatively high (e.g. radiant fluences in the range of between 2 J/cm$^2$ and 100 J/cm$^2$ have been previously discussed). In order to achieve these light fluences, light sources such as lasers or flash lamps were widely discussed. The use of LEDs as light sources was discussed as well, in particular for skin treatments such as wrinkle reduction or acne treatment, where the required light flux allows for using standard LEDs.

In particular for cosmetic light-based hair removal, the skin may considerably heat and may even heat to an unacceptable level if the skin pigmentation level is too high. It is known that some skin treatment devices for hair removal first measure the skin color and then automatically apply a light fluence per light pulse that leads to acceptable heat generation in the skin.

It is an object of the present disclosure to provide a skin treatment device that is improved over the known skin treatment device or that at least provides an alternative over known devices.

SUMMARY OF THE INVENTION

In accordance with one aspect there is provided a skin treatment device having at least a first LED, at least a first controllable current source, in particular a first controllable constant current source, for driving the first LED, a control unit for controlled switching of at least the first controllable current source between a first state in which current is provided to the first LED and a second state in which no current is provided to the first LED, and at least a first current sensor that is connected or connectable with the first LED so that the first current sensor and the first LED form a current path at least in the second state of the first controllable current source.

BRIEF DESCRIPTION OF THE DRAWINGS

The proposed skin treatment device is further elucidated by a detailed description of example embodiments, in particular with reference to figures. In the figures:

FIG. 1A shows a first state of the circuit in which the first LED is driven and emits light;

FIG. 2A shows a first state in which the first LED and the first parallel LED are driven and emit light;

FIG. 3 is a schematic cross-sectional depiction of an example head section of a proposed skin treatment device comprising two LEDs and a light-guide structure, where three example light path' are shown to exemplify the function of the head section;

DETAILED DESCRIPTION OF THE INVENTION

Figure 1A:
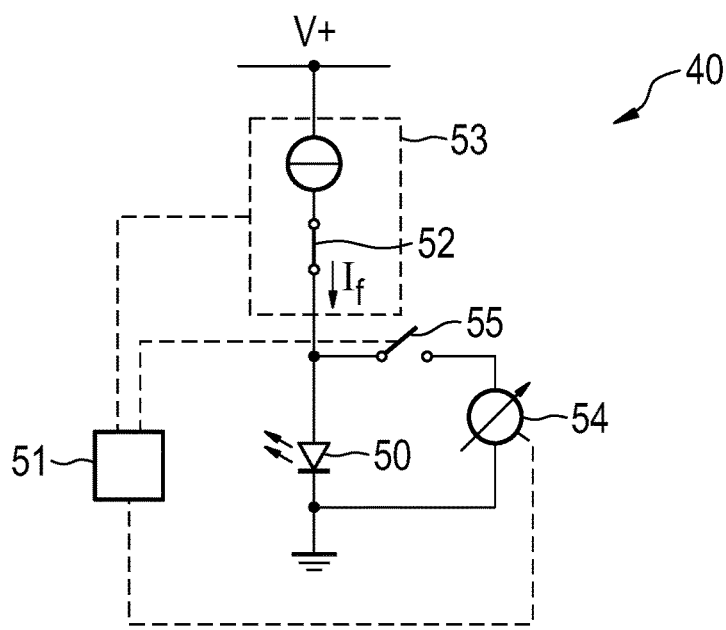
FIG. 1A is a schematic depiction of an example circuit to be used in a proposed skin treatment device for controllably driving a first LED and for reading out a photocurrent generated by the first LED, where

It is generally known that various types of skin treatment can be affected by applying light (in particular in the form of at least one treatment light pulse, often by applying a series of light pulses to one skin area or successively to adjacent skin areas) to the skin. Such skin treatments encompass skin rejuvenation, wrinkle reduction, acne treatment, and (temporal and permanent) hair removal (also named hair growth reduction or hair growth management, as hairs are not necessarily immediately removed by the application of intense light). In particular, skin treatment for achieving temporal and/or permanent hair removal (hair growth reduction—in the following just the term "hair removal" is used, but this term shall encompass all light-based hair removal applications) requires a radiant flux emitted by the light source per unit area that is much higher than the radiant flux that is required for skin rejuvenation or the like (even though the light fluence applied to a skin area may be similar, but then the light pulse is applied over a longer period of time). For the application of a treatment light pulse (or pulses) onto the skin, various light sources have been discussed such as laser light sources, flash lamps (e.g. Xenon arc lamps), and semiconductor light sources such as LEDs. While laser light sources and flash lamps have been widely discussed with respect to hair removal, the application of LEDs as light source has been discussed in much less detail, in particular as the required radiant fluence to be applied on the skin within a short pulse length (e.g. below 10 ms) is easily delivered by lasers or flash lamps. In contrast, the present disclosure is directed to surface emitting semiconductor light sources (where in the following the term LED is used, this shall encompass other solid state light sources such as VCSELs, VECSELs, or OLEDs, but not classical edge emitting semiconductor lasers). In particular arrays of LED dies (i.e. semiconductor dies in contrast to packaged LEDs), and their use for light-based temporal or permanent hair removal is considered. While the term LED is used in the following, this term may refer to an LED die (e.g. mounted on a substrate) rather than an individually packaged LED, as an array of individually packaged LEDs may not be able to provide the radiant flux needed for a specific skin treatment such as hair removal (but may provide a radiant flux sufficient for other skin treatments).

Reference is made to European patent applications 16153812.9 and 16153813.7, the content of which is incorporated herein by reference. In these two applications, the use of arrays of LED dies for skin treatment and in particular hair removal is discussed. LEDs are available that can emit light at essentially any wavelength from ultraviolet (UV) light to infrared (IR) light, i.e. from about 280 nm to about 1300 nm, e.g. depending on the used semiconductor material. LEDs suitable for hair removal may in particular emit in a range of between 490 nm to 1000 nm, further in particular they may emit in the far red and near infrared range of between 700 nm and 900 nm. An LED emits light with a relatively narrow spectral bandwidth of typically $\Delta\lambda \cong \pm \lambda/20$. Where in the present disclosure the term "wavelength" is used in relation to an LED's light output, this wavelength means the peak emission wavelength, i.e. the wavelength at the maximum of the light emission curve of the LED.

As has been mentioned above, the radiant flux used for hair removal is relatively high and bears the risk that home use and/or use by untrained personal may lead to overheating of the skin and thus burns of the skin. It is known that the skin pigmentation level of the skin plays a major role in the heat generation process in the skin as the melanin in the skin, which causes the skin color, strongly absorbs light, in particular in a wavelength range of between 650 nm to 1000 nm, where the light absorption coefficient of hemoglobin (i.e. blood) or water ($H_2O$) is much lower. It is thus generally known that the skin pigmentation level influences the applicable light intensity for avoiding skin burns while still enabling hair root coagulation. It had been discussed before to measure the skin color or skin pigmentation level and to control the light emission based on the measurement result in order to provide for automated skin overheating prevention.

In the present disclosure, it is proposed to make use of LEDs (which may be individually packaged LEDs, but particularly arrays of LED dies in order to achieve high radiant flux per unit area) as light emitters and in particular to use at least one LED for a dual purpose, i.e. using the LED as light emitter and as light detector. As a consequence, no further dedicated skin color sensor(s) is (are) necessary as the skin color measurement can be enabled by one (or more) of the LEDs that are also used to provide the skin treatment pulse. For sake of clarity, it is stated that the proposed skin treatment device may comprise only one LED, but it is also contemplated that the proposed skin treatment device comprises a plurality of LEDs and least one LED is then used for the mentioned dual purpose (alternatively, a plurality or all LEDs may be used for the dual purpose). In consequence, the skin color measurement essentially happens at the position where the treatment pulse will be applied (assuming that the device is not considerably moved between measurement and treatment pulse emission). Further, as will be explained in more detail below, also a spatially resolved skin color measurement is enabled if a plurality of LEDs is used. This allows automated setting of an overall radiant flux and/or radiant fluence provided by the treatment pulse and in particular spatially resolved controlling of the light application. Light concentrator units may be used to deliver the light of each of the LEDs onto an associated area of the user's skin and vice versa, namely concentrating the light emitted from a particular area of the user's skin onto an essentially uniquely associated LED. In this manner it can be assured that (natural or artificial) local peaks of the skin pigmentation level (e.g. liver spots or tattoos) can be treated with lower radiant fluence values or can even be excluded from illumination.

A LED die being a piece of semiconductor material is as such not only suited to emit light (when the right current flows through the LED die) but is also inherently sensitive to light impinging onto the semiconductor material. While dedicated photodiodes are offered for light detection, any LED die also provides a light sensitive effect. A LED die, when not being driven in the forward direction can be used as photo sensor: light (of the right wavelength) impinging onto the semiconductor die will generate electron-hole pairs and thus generates a small current flowing in reverse direction through the LED as soon as a current path is provided, which current is essentially linear with respect to the light intensity.

A skin treatment device as proposed in the present disclosure thus has at least a first LED that can be used by a control unit to fulfil the mentioned dual purpose. As will be discussed in more detail further below, the first LED (a "dual purpose LED") is provided in a circuit that can be switched between driving the first LED in forward direction (the first LED then acts as light emitter) and reading out a photocurrent via a respective other current path (the first LED then acts as light detector). Respective circuitry elements like a first controllable current source and a first current sensor are part of such a circuit.

In some embodiments, a proposed skin treatment device comprises at least a first LED, at least a first controllable current source, a control unit, and at least a first current sensor. The first LED may in particular be suited for emitting light pulses at a high light flux suitable for skin treatment, in particular for hair removal. Such a first LED may in particular have a radiant flux of at least 0.1 Watt (e.g. at least 0.2 W or at least 0.4 W), in particular where the radiant flux lies in a range of between 0.2 W and 5.0 W. In some embodiments, where a plurality of LEDs is used, the first LED may not be suitable for emitting a treatment light pulse at a high radiant flux, but the first LED may then be suited for emitting low radiant flux light, e.g. for indication purposes (the first LED may then be driven at a radiant flux of below 0.1 Watt (e.g. 0.05 W or 0.02 W), in particular in a range of between 0.001 W and 0.1 W. Such an indicator LED may be used to visually indicate the size of the active treatment area of an array of treatment LEDs.

The control unit is coupled with the first controllable current source so that the first controllable current source can be switched between a first state in which the first controllable current source delivers a (in particular predetermined or controllable) current for driving the at least first LED and a second state in which the first controllable current source does not deliver any current to the first LED. The first controllable current source may in particular comprise a switch in the current part (e.g. realized as a transistor, a FET or a MOSFET) to control the level of the delivered current. In some embodiments, a further separation switch may be arranged between the first controllable current source and the first LED, e.g. in embodiments where a further parallel LED is arranged in a circuit branch parallel to the first LED, which parallel LED is also driven by the first controllable current source (further details are discussed below).

The first current sensor is connected or connectable with the first LED to form a (closed) current path at least in the second state of the first controllable current source. In the second state of the first controllable current source, when the first LED is not driven, light exposure of the first LED leads to the generation of a small photocurrent in reverse direction, which reverse current flows then through the (closed) current path and thus through the first current sensor. The first current sensor may then be arranged to provide a first signal that is indicative of the magnitude of the reverse photocurrent generated by the first LED under light exposure and thus to provide a first signal allowing detecting different light exposure levels. The first current sensor may be connected with the first LED and may have a high ohmic resistance, so that essentially no current flows through the first current sensor when the first LED is driven. Alternatively, the first current sensor is arranged to be connectable to the first LED, e.g. by providing a connection switch that is coupled with the control unit between the first LED and the first current sensor in order to close a current path at least in the second state of the first controllable current source and to open it in the first state of the first controllable current source. By the proposed design, a first current path is present to drive the first LED in forward direction and a second current path is present, when the first current path is disabled, in order to read out a photocurrent flowing in reverse direction through the first LED.

The first signal provided by the first current sensor may in particular be delivered to the control unit and the control unit may set the radiant fluence and/or radiant flux to be delivered by the first LED in a next treatment pulse based on the first signal. In operation, the first signal is sensitive to the amount of light "seen" by the first LED. If a light source is present (either another LED or a general light source) that illuminates the skin (but not the first LED), the amount of light reaching the first LED is a measure of the skin pigmentation level as the light has to travel through the skin optically assigned to the first LED. As will be explained in more detail further below, the skin treatment device may comprise a plurality of LEDs (in some embodiments these may be arranged in a regular M times N matrix) so that a spatially resolved skin pigmentation level can be determined and local peaks in skin pigmentation such as tattoos or liver spots can be excluded from illumination by the next treatment pulse, e.g. if the respective LEDs are switched off during the next treatment pulse.

In some embodiments, at least a first parallel LED is present in addition to the first LED, which first parallel LED is arranged in a circuit branch parallel to the circuit branch of the first LED. The first controllable current source may be used to drive both LEDs, but in an alternative a second controllable current source is provided in the parallel branch to independently drive the first parallel LED. In addition or alternatively, a second current sensor may be connected or connectable with the first parallel LED so that a (closed) current path can be formed between the first parallel LED and the second current sensor as was already described for the first LED and the first current sensor.

The control unit may have two modes to control the first and second controllable current sources. In a first mode, the first LED is driven to emit light and the first parallel LED is as well driven to emit light (so that the LEDs provide a treatment light pulse). In a second mode, the first parallel LED is driven to emit light, typically at a lower radiant flux than is used in the treatment pulse, and the first LED is connected with the first current sensor and a photocurrent is read out by the first current sensor, so that a first signal indicative of the light exposure level of the first LED can be sent by the first current sensor to the control unit, which control unit may then set at least the radiant flux of the first LED to be applied in the next treatment pulse. Here, the control unit may also set the radiant flux (the pulse period may be fixed) to be applied by the first parallel LED in the next treatment pulse as the light path between the two LEDs comprises the skin pigmentation of the skin optically assigned to both LEDs.

In some embodiments, the skin treatment device comprises at least a first series-connected line of LEDs, which line comprises the first LED and at least a second LED. Additionally, at least a first parallel LED may be arranged in a circuit branch parallel to the circuit branch comprising the first line of series-connected LEDs or a at least a second line of series connected LEDs, which comprise the first parallel LED, may be arranged in such a parallel circuit branch. Generally, a plurality of more than two parallel circuit branches may be arranged, each comprising at least one LED, where in each branch a different number of LEDs may be present, but alternatively each parallel circuit branch may comprise the same number of LEDs, so that such a circuit may be characterized as an M times N matrix arrangement of LEDs, where M is the number of parallel circuit branches and N is the number of series-connected LEDs in each such parallel circuit branch.

In embodiments with at least a first series-connected line of LEDs, each of the LEDs of the first series-connected line of LEDs may have a short-circuiting switch arranged parallel to the respective LED so that in a read-out mode the photocurrent of selected LEDs can be short-circuited, in particular so that successively only one LED of the LEDs of the first series-connected line of LEDs is not short-circuited and its photocurrent can then be measured by a respective first current sensor arranged in a closed current path with the first series-connected line of LEDs (so-called multiplexing of the series-connected LEDs). The short-circuiting switches are in particular controllable by the control unit.

Generally, the first LED (or a plurality or all LEDs) of the skin treatment device used in the emission of the at least one treatment light pulse and/or measurement of photocurrents and/or used for indication purposes may be realized as a LED die that may in particular be mounted on a carrier such as a PCB, in particular the carrier may be a ceramic carrier and further in particular, the carrier may be a heat-conductive carrier (e.g. a ceramic-plated metal carrier).

In some embodiments, the skin treatment device comprises a light concentrator unit that is arranged so that light emitted by the first LED is essentially concentrated via an entrance area on the light concentrator unit to an exit area of the light concentrator unit. Additionally or alternatively, the light concentrator unit is arranged to concentrate light entering via the exit area (e.g. light exiting the skin) via the entrance area onto the first LED. Without being bound by theory, such a light concentrator unit may concentrate up to about 80% of the light emitted by the first LED to the exit area.

In some embodiments, a skin treatment device comprises a light pass window and a lens mounted at or near the light pass window so that light entering through the light pass window at the location of the lens is essentially concentrated onto the first LED. In case of a plurality of LEDs, a lens array may be used, where each lens of the lens array is uniquely assigned to one of the LEDs.

In the following, several example embodiments in accordance with the present disclosure are discussed.

Example 1: Single LED Used for Light Emission and Light Detection

Figure 1B:
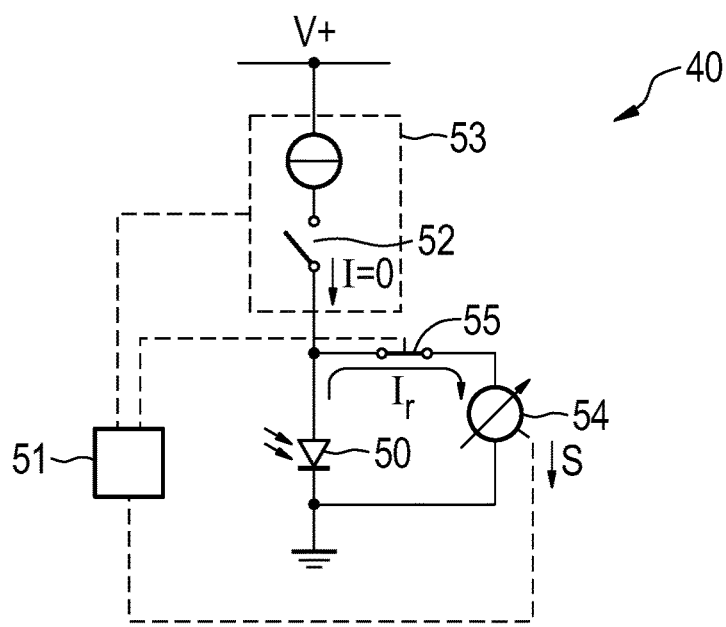
FIG. 1B is a schematic depiction of a second state of the circuit shown in FIG. 1A, where a photocurrent generated by the first LED due to light exposure is sensed by a current sensor.

In a first example shown in FIGS. 1A and 1B, an electronic circuit 40 of a skin treatment device as proposed is schematically shown that comprises a first LED 50, a control unit 51, a first controllable current source 53, and a first current sensor 54. A further first connection switch 55 coupled with the control unit 51 is present as well, but this first connection switch 55 for forming a closed current path between the first LED 50 and the first current sensor 54 is optional and can be discarded if the first current sensor has, e.g., a high ohmic resistance. FIG. 1A shows a state of the electronic circuit 40 in which the first LED 50 is used as a light emitter and FIG. 1B shows a state of the electronic circuit 40 in which the first LED 50 is used as a light detector. In FIG. 1A, the first controllable current source 53 is switched by the control unit 51 in a first state in which it provides a forward current $I_f$ that flows through the first LED 50. The first controllable current source 53 may comprise a switch 52 (e.g. realized by a transistor, a FET or a MOSFET) that is controlled so that the driving current $I_f$ is provided—in FIG. 1A this is indicated by a "closed" switch 52, which means that a respective transistor of the current source would be "on". The first current source 53 may be realized as a first controllable constant current source. The current $I_f$ is sufficient for the semiconductor material of the first LED 50 so that electron-hole pairs can recombine under the emission of light. The first current sensor 54 is disconnected in FIG. 1A from the first controllable current source 53 by an opened connection switch 55 or, alternatively or additionally the first current sensor 54 may be built up in way that it does not short circuit the current from the first controllable current source 53. The first current sensor 54 is here coupled with the control unit 51.

In the state shown in FIG. 1B, the control unit 51 has switched the first controllable current source 53 into its second state in which it does not create any current for the first LED 50. The switch 52 is shown as "open", which means that a respective transistor realizing switch 52 would be "off", i.e. is not allowing current to flow. The first connection switch 55 is closed. The first LED 50 and the first current sensor 54 then form a closed current path. Once light of the right wavelength to generate electron-hole pairs impinges onto the semiconductor material of the first LED 50, a reverse current $I_r$ is generated that flows through the first current sensor 54. The first current sensor 54 is arranged to provide a first sensor signal S that is indicative of the level of the reverse current $I_r$ and thus represents a measure for the intensity of the light exposed on the first LED 50.

The first current sensor 54 may be realized in any suitable manner and may provide as first sensor signal S a current signal, a voltage signal, or a digital signal. The first current sensor 54 may, inter alia, comprise a Hall-effect sensor, a transformer, or a resistor or the input of an amplifier. The first current sensor 54 may in particular be arranged as a current-to-voltage converter unit (e.g. as a trans-impedance amplifier). The first sensor signal S is here provided by the first current sensor 54 to the control unit 51, which may control the first current source 53 in dependence on the first sensor signal S so that the light flux provided by the first LED 50 in a next light emission mode (in particular for the next treatment pulse emission) is controlled.

Example 2: Two LEDs Arranged Parallel to Each Other

Figure 2A:
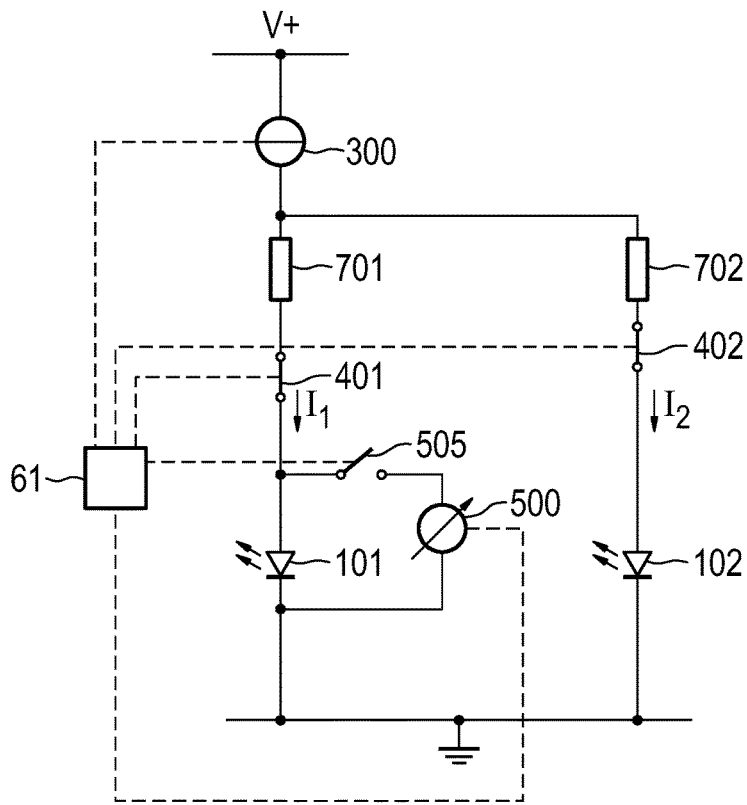
FIG. 2A is a schematic depiction of another example circuit to be used in a proposed skin treatment device for controllably driving a first LED and a first parallel LED, where
Figure 2B:
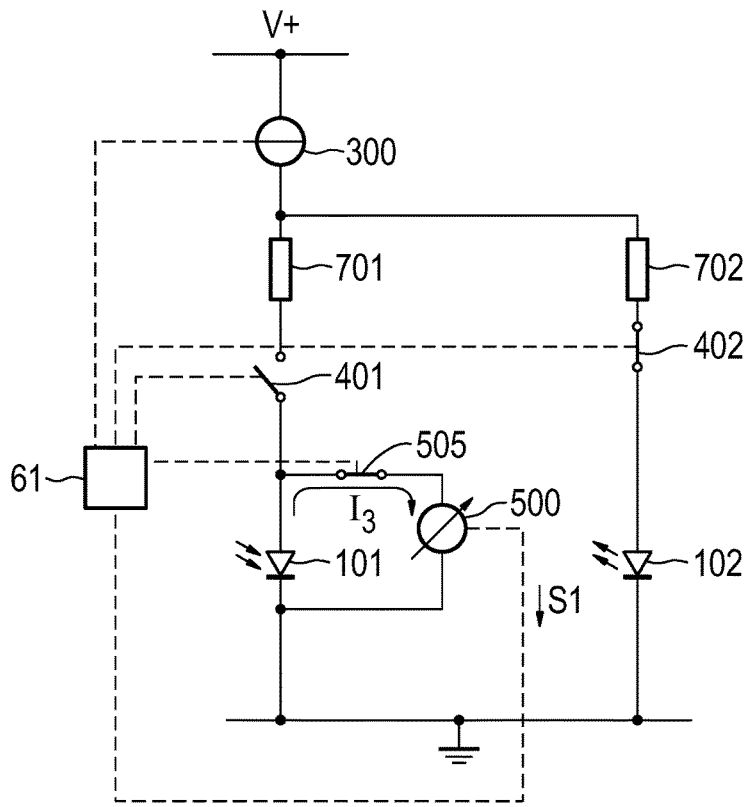
FIG. 2B is a schematic depiction of the circuit shown in FIG. 2A, where only the first parallel LED is driven and the first LED forms a current path with a first current sensor for reading out a photocurrent generated by the first LED.

In a second example embodiment as shown in FIGS. 2A and 2B, an electronic circuit 41 is shown comprising a plurality of LEDs 100 that encompass a first LED 101 and a first parallel LED 102 that are both driven by a first controllable current source 300 (for sake of simplicity, no further switch is shown to visualize the state of the first controllable current source). The first LED 101 is connectable to and separable from the first controllable current source 300 via a first controllable separation switch 401 and the first parallel LED 102 is connectable to and separable from the first current source 300 via a second controllable separation switch 402. The first and second controllable separation switches 401, 402 are connected with a control unit 61 for controlled opening and closing of the first and second controllable separation switches 401, 402. Each of the LEDs 101, 102 has a protection resistor 701 and 702, respectively, to protect from too much current drawn by one LED. The use of protection resistors may not be necessary in case that separate controllable current sources are used. In FIG. 2A, the first and second controllable separation switches 401 and 402 are closed and a current L flows through the first LED 101 and a current $I_2$ flows through the first parallel LEDs 102. The applied voltage range of the current sources is selected to be high enough so that the voltage over the LEDs 101, 102 causes the LEDs to emit light, where the intensity of the emitted light is depending on the height of the current flowing through the respective LED. The first LED 101 and the first parallel LED 102 are used in FIG. 2A as light emitters. The LEDs 101 and 102 may both be arranged to emit in the infrared (IR) wavelength range, e.g. at 850 nm (the minimum bias voltage to generate light emission is then about 1.5 V). The emitted radiation may be used for treating the skin of a user, e.g. for acne treatment, wrinkle reduction, or hair removal. A first current sensor 500 that may be realized as a current-to-voltage conversion unit is connectable with the first LED 101 to form a closed current path when the first LED is used as a photo detector (FIG. 2B), comparable to FIG. 1B. Again, the optional first connection switch 505 is shown in an open state. As shown in FIG. 2A, the control unit 61 controls the electronic circuit 41 so that each of the LEDs 101 and 102 is used as a light emitter.

FIG. 2B shows a state of the electronic circuit 41 in which the control unit 61 has opened the first controllable separation switch 401 so that a current provided from the current source 300 cannot flow through the first LED 101. The first LED 101 is thus disabled as light emitter. As was already explained, the first LED 101—as a semiconductor device— is generally sensible to ambient light as ambient light can generate electron-hole pairs in the semiconductor (if the light has the right energy or wavelength). A small current $I_3$ then flows in reverse direction through the first LED 101 when ambient light impinges onto the first LED 101 (i.e. onto the semiconductor die of the LED). The current $I_3$ is essentially linearly depending on the light intensity. The first LED 101 can thus be used as a light detector in the state shown in FIG. 2B. The first current sensor 500 can be used to generate a first sensor signal S1 that is indicative of the height of the current $I_3$, which first sensor signal S1 may then be used for further analysis, e.g. the first sensor signal s1 may be fed into the control unit 61. The first sensor signal S1 may in particular be fed into an analog-to-digital converter (ADC) so that a digital value may be used in the further processing of the first sensor signal S1. As the reverse current $I_3$ flowing in light detection mode is relatively small, in particular a trans-impedance amplifier may be used as first current sensor 500. The first parallel LED 102 is in this mode still used as a light emitter (the radiant flux of the first parallel LED may be set to a low value only suited for illumination purposes, but not for skin treatment purposes).

With respect to the first LED, the first controllable current source 300 (seen in combination with the first controllable separation switch 401) is understood to be in a first state in FIG. 2A, where a driving current is provided at the first LED, and in a second state in FIG. 2B, where no current is delivered to the first LED.

FIG. 3 is a schematic depiction of an example head section 11 of a skin treatment device. The head section 11 comprises a first LED 101A and a first parallel LED 102A, e.g. the LEDs 101 and 102 discussed with reference to FIGS. 2A and 2B. The head section 11 further comprises a light concentrator unit 800 (may also be called a light guide) for guiding light emitted from the LEDs 101A, 102A to a skin surface 1000 (here, the head section 11 is shown as directly contacting the skin 1000, which is the natural operation state of the skin treatment device, even though the skin treatment device may also work at a predetermined distance; the skin treatment device may inhibit at least treatment light emission if the head section 11 is not in contact with the skin). The light concentrator unit 800 is also suited to guide light emitted from the skin surface to the LEDs 101A and 102A. The light concentrator unit 800 comprises two lens sections 801 and 802, which are each uniquely associated with one of the LEDs 101A and 102A, respectively. The head section 11 further comprises a frame 920 and a light pass window 910, e.g. realized by a transparent (synthetic) sapphire glass window. It is here indicated that a skin contact sensor 931 may be arranged in the frame 920 (the skin contact sensor 931 may comprise a single sensor element or may comprise a plurality of sensor elements). As was indicated before, the skin treatment device may inhibit the emission of light if skin contact is not detected or if the distance to the skin does not fall below a certain predetermined threshold distance. The skin contact sensor 931 may be realized as a capacitive sensor, as an optical reflex sensor, or as a mechanical switch that is activated by pressing the skin contact sensor 931 onto the skin.

Each of the lens sections 801 and 802 has respective top and bottom light entry surfaces 801A, 801B and 802A, 802B. The top light entry surfaces 801A and 802B are arranged close to the two LEDs 101 and 102, respectively, so that the light emitted by the two LEDs 101A and 102A is collected by these light entry surfaces 801A, 802A. The light emitted by the second LED 102A is collected by light entry surface 802A and is delivered (i.e. concentrated) via light entry surface 802B (then serving a light exit surface) onto skin area A2 as indicated in FIG. 3. Three possible light paths P1, P2, and P3 are shown in FIG. 3. Light Path P1 is an example light beam (e.g. a single photon) emitted by the second LED 102A that is scattered within the skin so that the light travels towards a neighboring skin area, where it scatters again, so that the light is emitted at the skin surface relating to skin area A1, where the light emitted at skin area A1 is concentrated via the lens element 801 onto the first LED 101A. Light path P2 is an example of light emitted by the LED 102A that is guided by the lens element 802 of the light concentrator unit 800 onto skin area A2, where the light is scattered in the skin and travels outside of the skin areas A1 and A2. Finally, light path P3 shows light being emitted by the LED 102A that travels into the skin, where it becomes absorbed. Obviously, arbitrary light paths exist and the shown light paths P1, P2, P3 are just shown to illuminate the general concept. It is clear, that light that would eventually reach the first LED 101A has a high probability of becoming absorbed (as shown by light path P3) in the skin if the skin pigmentation level is high. The amount of light reaching the first LED 101A is thus a measure of the skin pigmentation level in skin areas A1 and A2.

A strong local skin pigmentation level (e.g. caused by a tattoo) covering the skin area A1 or A2 causes then a low reverse current through the first LED 101A, but also a low current would be measured through the first parallel LED 102A when the first parallel LED 102A were used as light detector and the first LED 101A as light emitter. As a consequence, the control unit would switch off LED 101A and LED 102A during the next treatment pulse period. If the strong local skin pigmentation only partly covers the skin area associated with one of the LEDs, while no local strong skin pigmentation is present at the skin area associated with the other LED, both LEDs 101A and 1102A may be used in the next treatment pulse period. Assuming the resolution size of the LEDs to be about 1 mm$^2$, a partial coverage of strong pigmented skin by a treatment pulse (e.g. covering an area of about 0.5 mm$^2$) is generally not harmful as the heat generated in such a small skin area can be distributed fast to cooler neighboring skin areas. The treatment pulse would be (locally) reduced or switched off if the strong pigmentation level covers a larger area, in particular the complete area associated with one of the LEDs 101A or 102A (in some embodiments this may be a skin area of about and above 1 mm$^2$).

Ways of using at least the first LED as light detector and how this can be utilized to control the skin treatment device are explained in the following.

As was explained in detail with reference to FIG. 3, a light concentrator unit may be used to concentrate light emitted by, e.g., the first parallel LED 102A (LED 102 in FIGS. 2A and 2B) onto an area of the skin of a user (that means: in operation, when the skin treatment device is placed onto the skin of the user), where the light will travel via scattering processes into neighboring skin areas. The scattered light will eventually exit the skin in these neighboring areas again and can then be concentrated via a lens (which may be a part of the light concentrator unit) onto, e.g., LED 101A, which, when controlled as shown in FIG. 1B, can then measure the intensity of the light emitted from the respective skin area associated with said lens. Thus, first LED 101A is here utilized as a first dual-purpose LED.

Depending on the general skin pigmentation and further depending on local skin pigmentation differences (as may be caused by liver spots or tattoos), the amount of light reaching LED 101A (or in other words: the ratio of the light flux received by LED 101A and the light flux emitted by LED 102A) is a measure of the skin pigmentation level essentially at the location of the measurement. The current $I_3$ generated by the light impinging onto LED 102 (FIG. 2B) is thus indicative of the skin pigmentation level and can be used to control the light emission of the plurality of LEDs 100 in a next treatment pulse that may be applied after the measurement of the skin pigmentation level. A high skin pigmentation level may thus lead to a controlled reduction of the emitted light flux to avoid burning of the skin via too strong light absorption. The control unit 61 may thus first drive the plurality of LEDs 100 as shown in FIG. 2B in order to measure the skin pigmentation level, may then determine a light intensity to be emitted in a treatment pulse (that means: determination of the current level provided at the LEDs 101 and 102), and may then control the plurality of LEDs 100 as shown in FIG. 2A in order to apply the treatment pulse by providing currents I1 and I2 adapted to the measured skin pigmentation level. The light flux emitted by LED 102 used for the skin pigmentation level determination as shown in FIG. 2B may in particular be lower than a typical treatment light flux. The emission of treatment light by the plurality of LEDs 100 may even be switched off if the measured skin pigmentation level is too high for risk-free treatment (which may be the case for naturally or artificially strong pigmented skin).

In some embodiments, a current-to-voltage conversion unit is also present for LED 102, so that also LED 102 can then be utilized as a dual-purpose LED.

Example 3: Two LEDs Arranged in Series

Figure 4A:
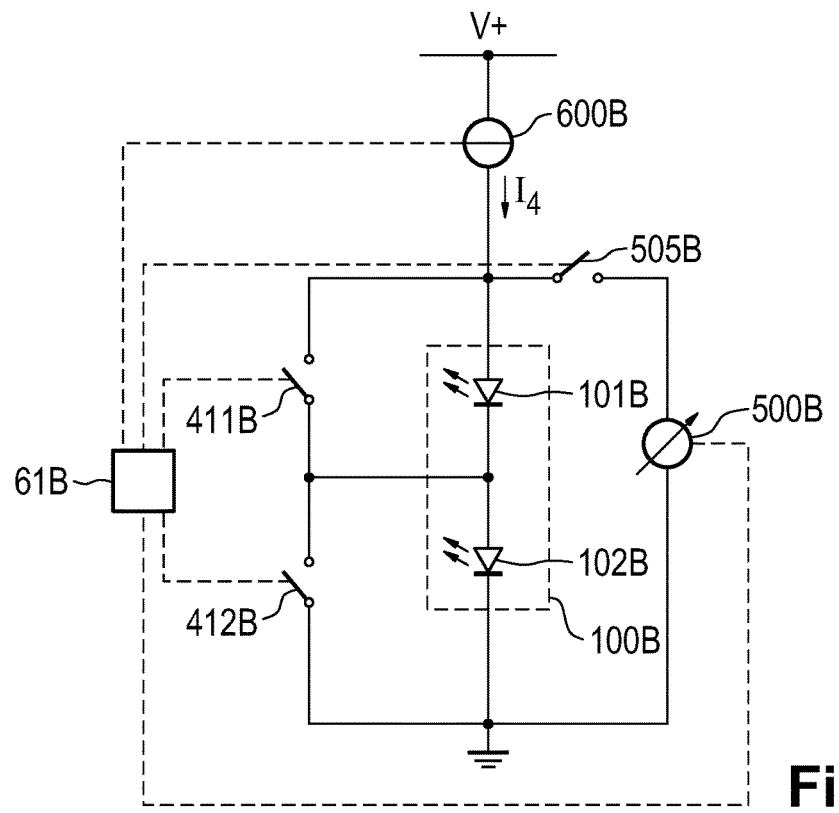
FIG. 4A is a schematic depiction of a further example circuit to be used in a proposed skin treatment device for controllably driving a first series-connected line of LEDs shown in a first state in which the series-connected LEDs are driven to emit light and where each of the series-connected comprises a parallel short-circuiting switch.

FIGS. 4A and B show an example electronic circuit 42 with a first line of series connected LEDs 100B, which comprises a first LED 101B and a second LED 102B that are arranged in series. In this example, the first line of series connected LEDs 100B is connected with a first controllable current source 600B, which provides a current $I_4$ when it is enabled (i.e. is in the first state). A control unit 61B is controllably connected with a first and a second controllable short-circuiting switch 411B, 412B. The first controllable short-circuiting switch 411B is connected in parallel with only the first LED 101B and the second controllable short-circuiting switch 412B is connected in parallel with only the second controllable short-circuiting switch 412B. Further, a first current sensor 500B that may be realized as a current-to-voltage conversion unit is arranged connectable with the first line of series connected LEDs 100B in order to form a closed current path—a controllable connecting switch 505B is present. In FIG. 4A it is shown that the first LED 101B and the second LED 102B are used as light emitters; current is delivered from the first controllable current source 600B being in its first state. The first and second controllable short-circuiting switches 411B and 412B are open. A constant current $I_4$ is flowing through the LEDs 101B and 102B and the available voltage V+ is sufficient so that the LEDs 101B and 102B emit light.

Generally, the leads connecting the LEDs in the circuit path in which the (constant) current flows are arranged to accommodate large size currents such as 1 Ampere (A), in particular of up to about 4 A. The leads connecting the LEDs with the controllable short-circuiting switches in the circuit path in which the short-circuited reverse current flows or the leads connecting the first current sensor with the first line of series-connected LEDs 100B only need to accommodate the relatively small reverse current, which typically is below 10 mA. Thus, the additional circuitry relating to the light detection mode can be realized as being relatively small and may be realized on a small die placed just beneath the respective LED, e.g. the LEDs may be realized as LED dies placed on a (ceramic or ceramic-plated) carrier and the circuitry for light detection may be realized as small (e.g. below 50 µm wide) lines on the carrier (or within a multi-layer carrier). This is generally valid for all herein discussed examples.

Figure 4B:
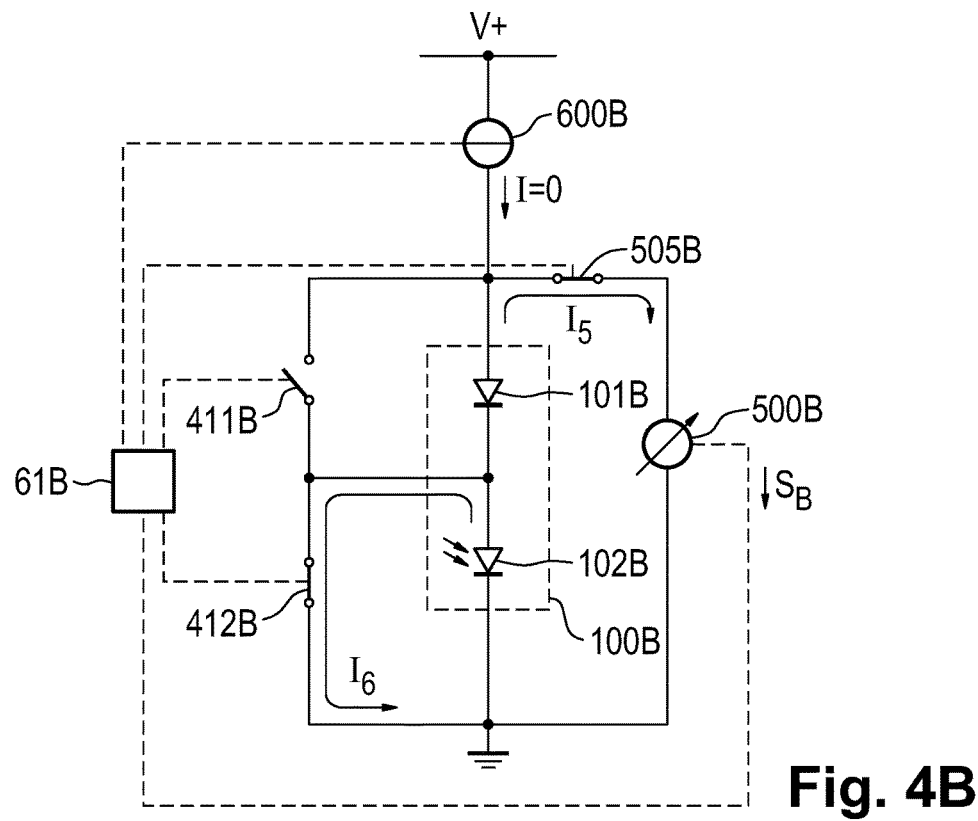
FIG. 4B is a schematic depiction of the circuit shown in FIG. 4A in a first alternative of a second state in which one of the LEDs is short-circuited while the photocurrent generated by another LED is read out by a current sensor.

In FIG. 4B the same electronic circuit 42 as in FIG. 4A is shown, but here the first controllable current source 600B has been switched into its second state by control unit 61B and thus the first controllable current source 600B does not provide a current. The first LED 101B is used as light detector. In the state of the circuit shown in FIG. 4B, the reverse current Is generated by the first LED 101B is read out by the first current sensor 500B and a first sensor signal $S_B$ indicative of the height of the reverse current $I_5$ flowing through the first LED 101B caused by light impinging onto the first LED 101B is generated by the first current sensor 500B. The reverse current $I_6$ generated by the second LED 102B when light is impinging onto the second LED 102B is short-circuited by the closed second controllable short-circuiting switch 412B and does thus not flow through the first current sensor 500B. The situation as shown in FIG. 4B may last for a certain time period that is necessary for generating the first sensor signal $S_B$. In a next step, control unit 61B may close the first controllable short-circuiting switch 411B and open the second controllable short-circuiting switch 412B so that during another time period a sensor signal representative of the amount of light impinging onto the second LED 102B can be determined by the first current sensor 500B. While the control unit 61B keeps the LEDs 101B and 102B in light detection mode, a separate light source (not shown) may be used to illuminate the skin.

It is generally and valid for all embodiments not necessary to drive the LEDs 101B and 102B with a reverse voltage, but in some embodiments a reverse voltage is applied at the LEDs 101B and 102B, which reverse voltage tends to reduce dark currents through the LEDs and to increase the signal-to-noise level and the frequency spectrum of the determined sensor signal.

Figure 5:
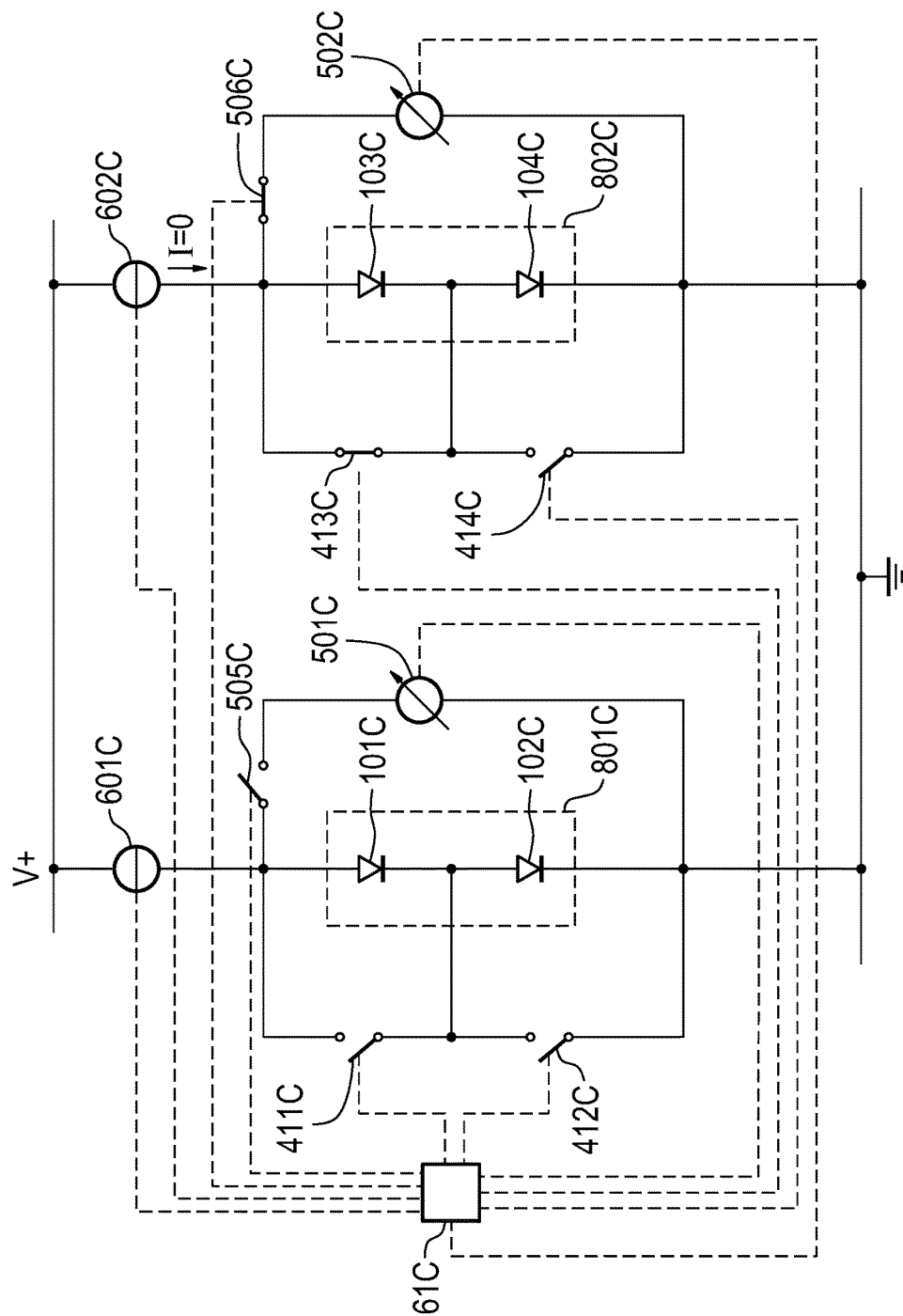
FIG. 5 is a schematic depiction of an even further example circuit for use in a proposed skin treatment device comprising two lines of series-connected LEDs.

Example 4: Two Series-Connected Lines of LEDs Arranged in Circuit Branches Parallel to Each Other FIG. 5 shows another example comprising a first series connected line of LEDs 801C and a second series-connected line of LEDs 802C. Each of the lines of series connected LEDs comprises two LEDs, so that the arrangement may be described as a 2 times 2 matrix arrangement of LEDs. In the first line of series connected LEDs 801C, a first LED 101C and a second LED 102C are arranged in series and in the second line of series connected LEDs 802C, a first parallel LED 103C and a second parallel LED 104C are arranged in series. The first and second series-connected lines of LEDs 8001C and 802C are connected to a first and a second controllable current source 601C and 602C, respectively. Further, each line of series-connected LEDs 801C and 802C comprises controllable short-circuiting switches 411C, 412C and 413C, 414C that are each connected in parallel to one of the LEDs as has been discussed with reference to FIGS. 4A and 4B. The controllable short-circuiting switches 411C, 412C, 413C, 414C are all connected with a control unit 61C. A first current sensor 501C is connected with the first series-connected line of LEDs 801C via a first controllable connection switch 505C to form a current path and a second current sensor 502C is connectable with the second series-connected line of LEDs 801C via a second controllable connection switch 506C. Thus, each of the lines of series-connected LEDs 801C and 802C is essentially a copy of the arrangement shown in FIGS. 4A and 4B. The plurality of LEDs arranged in the 2 times 2 matrix may also physically be arranged in a regular 2 times 2 matrix, but this is not a requirement and actually the LEDs may physically be arranged totally different from a matrix arrangement (e.g. randomly).

The following two modes may be controllable by the control unit 61C:

a) Treatment mode: the first and second controllable current sources are each in their first state (i.e. they provide a current to drive the respective LEDs in their assigned lines of LEDs) and the controllable short-circuiting switches 411C-414C are all open. A current is provided from the controllable current sources 601C and 601C and the LEDs 101C-104C emit light at a radiant flux sufficient for the intended treatment.

b) Light detection mode: one of the first or second controllable current sources 601C or 602C is disabled (i.e. is in its second state and does not provide a current)—then the respective other controllable current source is enabled (i.e. in its first state and provides a current). A relatively small constant current may be provided by the enabled controllable current source so that the LEDs of the respective line of series-connected LEDs driven by the enabled controllable current source emit light at a radiant flux sufficient for light detection by the LEDs of the respective other line of series-connected LEDs. The control unit 61C closes one of the controllable short-circuiting switches of the LEDs relating to the disabled controllable current source and keeps the other open, so that the reverse current flowing through the respective LED with the open controllable short-circuiting switch can be determined by the respective current sensor (while the reverse current flowing through the other LED is short-circuited as has been discussed with respect to Example 3 above). In order to receive scattered light of sufficient intensity for a reliable measurement, the LEDs may physically be arranged closely to each other. The control unit 61C may then open the closed controllable short-circuiting switch and close the other short-circuiting switch of the same line of LEDs in order to sample the reverse current of the other LED. The control unit 61C may then enable the so far disabled controllable current source and disables the so far enabled controllable current source controllable current source in order to successively read out the reverse currents from the other line of series-connected LEDs, while the driven line of series-connected LEDs emits light.

Example 5: M Times N Series-Connected LEDs Arrangement

Figure 6:
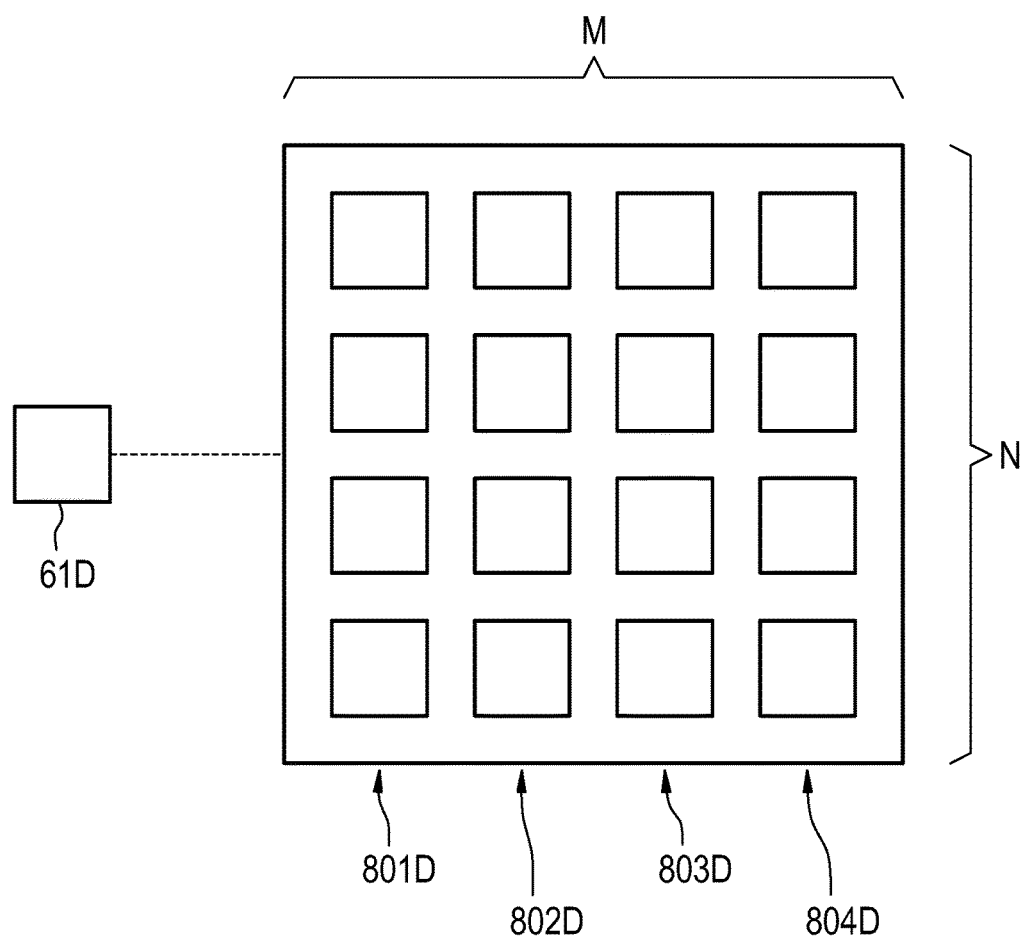
FIG. 6 is a schematic depiction of an M times N LED array (here 4 times 4) having M parallel lines of series-connected LEDs, where each line comprises N LEDs.

FIG. 6 is a schematic depiction of a 4 times 4 matrix arrangement of four lines of series-connected LEDs 801D-804D that each comprise four series connected LEDs. This shall be understood as one example of a general M times N arrangement, i.e. an arrangement with M lines of series-connected LEDs where each line has N series-connected LEDs. Other examples are, e.g., a 10 times 10 matrix arrangement or a 16 times 5 matrix arrangement, but generally the LEDs may be arranged in a matrix having an arbitrary size. Reference is made to FIG. 5, and it shall be understood that the controllable short-circuiting switches connected parallel with each LED and a current sensor for each of the lines 801D-804D are here present as well. As was explained above for Example 4, a control unit 61D can control the controllable switches so that successively the LEDs from the lines are read out, while the other lines are used to emit light. Alternatively, the control unit 61D may be arranged to successively read out the LEDs of every other line in parallel (which is possible as each line has its own current sensor) and then to switch to read out the respective other lines in parallel. A 10 times 10 matrix may be read out with a time period of less than 1 ms (a single LED may be read out within a time period of 1 μs). If the skin pigmentation level measurement is done just shortly before emission of a treatment light pulse (e.g. 1 ms before), the individual LEDs of the M times N array may be controlled to emit light with an radiation flux adapted to the measured spatially-resolved skin pigmentation levels, where in particular individual LEDs may be switched off completely if a local skin pigmentation level peak was determined (e.g. liver spot or tattoo).

Light Concentrator Units

Figure 7A:
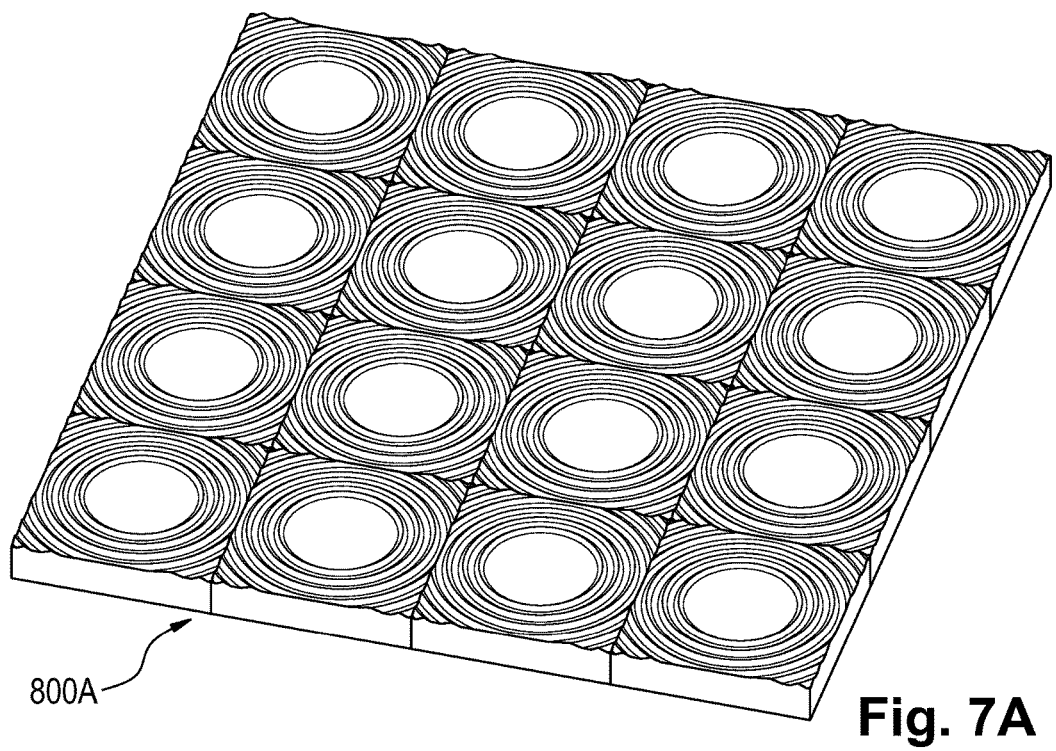
FIGS. 7A-7B are depictions of example light concentrator units.
Figure 7B:
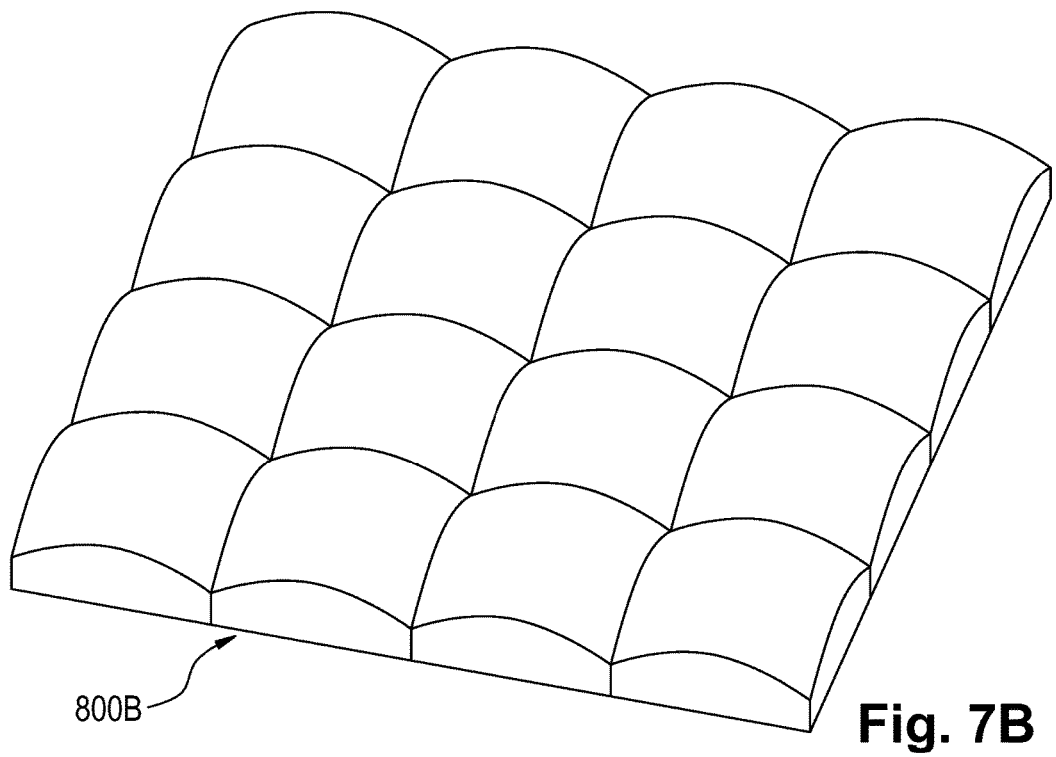

FIGS. 7A and 7B show two example realizations of light concentrator units 800A and 800B for a 4 times 4 arrangement of LEDs (which are physically arranged on a regular square pattern having the same dimensions as the light concentrator unit). FIG. 7A shows a realization where each LED can be associated with one Fresnel lens, which allows a particular thin construction. FIG. 7B shows a design of a light concentrator unit 800B with regular lenses. Obviously, in case the LEDs are arranged in a different pattern, the lenses of the light concentrator unit may just resemble the same pattern (e.g. a hexagonal or random pattern).

Skin Treatment Device

Figure 8:
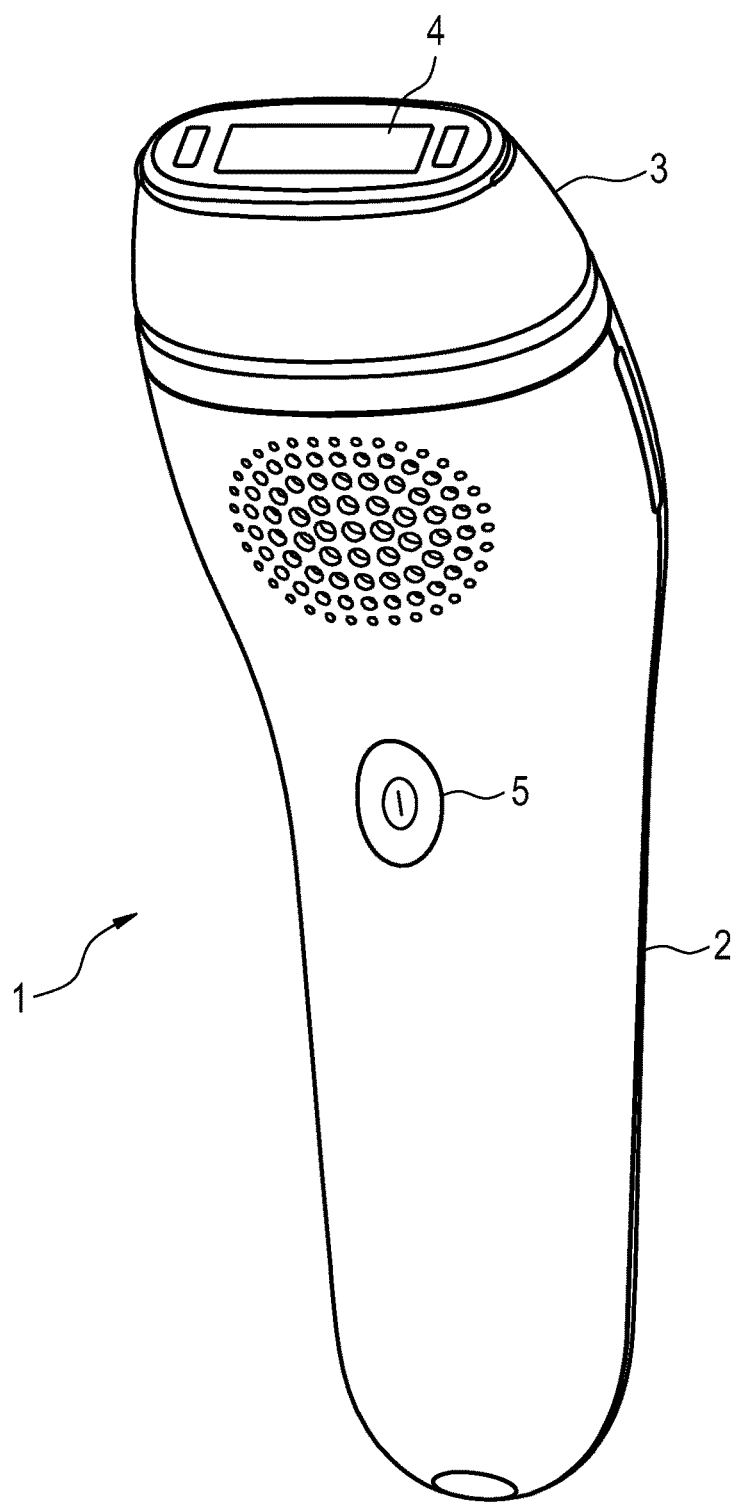
FIG. 8 is a schematic depiction of an example skin treatment device.

FIG. 8 is a schematic depiction of a skin treatment device 1 in accordance with the present description. The skin treatment device 1 has a housing 2 in which a rechargeable battery may be housed as well as control and drive circuitry for a plurality of LEDs. On one end of the housing 2, a head section 3 is arranged, has an exit window 4 through which light pulses can be emitted for treating the skin. The plurality of LEDs may be arranged behind the exit window 4. A control element 5 (e.g. ON/OFF switch) is arranged on the housing 2. The skin treatment device 1 comprises an electronic circuit as discussed in the present disclosure.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin treatment device comprising:
   at least a first LED capable of emitting light having skin treatment properties;
   at least a first controllable current source for providing a forward current for driving the first LED;
   a first controllable switch;

a second controllable switch;
a control unit for controlled switching of the first controllable switch between open and closed positions and for controlled switching of the second controllable switch between open and closed positions such that when the first switch is closed and the second switch is open the first controllable current source is in a first state in which forward current is provided to the first LED causing the first LED to emit skin treatment light and when the first switch is open and the second switch is closed, the first controllable current source is in a second state in which no forward current is provided to the first LED; and
at least a first current sensor connectable with the first LED and in the same circuit as the first LED and the second controllable switch so that the first current sensor and the first LED form a closed current path in the second state of the first controllable current source when the first controllable switch is open and the second controllable switch is closed so that the first current sensor receives reverse current from the first LED operating as a light detector.

2. The skin treatment device in accordance with claim 1, wherein the first current sensor is arranged to provide a first sensor signal that is indicative of the reverse current generated in the first LED in response to light exposure and flowing through the current path between the first LED and the first current sensor when the first controllable current source is in the second state.

3. The skin treatment device in accordance with claim 2, wherein the control unit is arranged to receive the first sensor signal and to set a radiant flux to be provided by the first LED when the first controllable light source is in the first state in dependence on the first sensor signal.

4. The skin treatment device in accordance with claim 1, comprising at least a first parallel LED that is arranged in a circuit branch parallel to the first LED and a second current sensor connectable with the first parallel LED so that the second current sensor and the first parallel LED form a current path.

5. The skin treatment device in accordance with claim 4, comprising a second controllable current source that is arranged in the parallel circuit branch for independently driving the first parallel LED, and the control unit is arranged for controlled switching of the second controllable current source between a first state in which current is provided to the first parallel LED and a second state in which no current is provided to the first parallel LED.

6. The skin treatment device in accordance with claim 5, wherein the control unit has a mode where during one time period the first controllable current source is in the first state and the first LED emits light, while the second controllable current source is in the second state and the first parallel LED and the second current sensor form a closed current circuit and the second current sensor is arranged to provide a second sensor signal that is indicative of a reverse current generated in the first parallel LED in response to light exposure and where during another time period the second controllable current source is in the first state and the first parallel LED emits light, while the first controllable current source is in the second state and the first LED and the first current sensor form a closed current circuit and the first current sensor is arranged to provide a first sensor signal that is indicative of a reverse current generated in the first parallel LED in response to light exposure.

7. The skin treatment device in accordance with claim 1, having a first series-connected line of LEDs comprising the first LED and at least a second LED and the first series-connected line of LEDs is connected with the first controllable current source, wherein the first current sensor is connectable with the first series-connected line of LEDs so that the first current sensor and the first series-connected line of LEDs form a current path at least in the second state of the first controllable current source.

8. The skin treatment device in accordance with claim 7, wherein a first controllable short-circuiting switch controllable by the control unit is connected in parallel with the first LED and a second controllable short-circuiting switch controllable by the control unit is connected in parallel with the second LED.

9. The skin treatment device in accordance with claim 8, wherein the control unit has a mode in which the first controllable current source is in the second state and where during one time period the first controllable short-circuiting switch is open so that a reverse current generated in the first LED flows through the current path to the first current sensor and the second controllable short-circuiting switch is closed so that a reverse current generated in the at least second LED is short-circuited and where during another time period the first controllable short-circuiting switch is closed so that a reverse current generated in at least the first LED is short-circuited and the second controllable short-circuiting switch is open so that a reverse current generated in the second LED flows through the current path to the first current sensor.

10. The skin treatment device in accordance with claim 7, comprising a second series-connected line of LEDs arranged in a circuit branch parallel to the first series-connected line of LEDs.

11. The skin treatment device in accordance with claim 1, comprising M series-connected lines of LEDs, where each of the series-connected lines of LEDs has N LEDs.

12. The skin treatment device in accordance with claim 1, wherein at least the first LED is a LED die that is mounted on a carrier.

13. The skin treatment device in accordance with claim 12, wherein the carrier comprises a heat-conductive ceramic carrier.

14. The skin treatment device in accordance with claim 1, further comprising a light concentrator unit, the light concentrator unit being arranged so that the light emitted by the first LED is guided by the light concentrator unit from an entrance area to an exit area.

15. The skin treatment device in accordance with claim 1, further comprising a light pass window and a lens mounted at or near the light pass window, which lens is arranged so that light entering through the light pass window at the location of the lens is concentrated onto the first LED.

16. The skin treatment device in accordance with claim 1, wherein the control unit has at least one mode in which the control unit is arranged to control the first LED to emit light at a radiant flux in a range of between 0.001 W and 0.10 W and another mode in which the control unit controls the first LED to emit light at a radiant flux in a range of between 0.2 W and 5.0 W.

* * * * *